US010954504B2

(12) United States Patent
Karbarz et al.

(10) Patent No.: US 10,954,504 B2
(45) Date of Patent: Mar. 23, 2021

(54) PREPARATION OF FACTOR XA DERIVATIVES

(71) Applicant: Alexion Pharmaceuticals, Inc., Boston, MA (US)

(72) Inventors: Mark Karbarz, South San Francisco, CA (US); Pamela B. Conley, Palo Alto, CA (US); Genmin Lu, Burlingame, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 16/740,001

(22) Filed: Jan. 10, 2020

(65) Prior Publication Data

US 2020/0208131 A1 Jul. 2, 2020

Related U.S. Application Data

(62) Division of application No. 15/626,813, filed on Jun. 19, 2017, now Pat. No. 10,604,748.

(60) Provisional application No. 62/351,841, filed on Jun. 17, 2016.

(51) Int. Cl.

| | |
|---|---|
| ***A61K 38/36*** | (2006.01) |
| ***C12N 9/64*** | (2006.01) |
| ***C07K 1/18*** | (2006.01) |
| ***C07K 1/20*** | (2006.01) |
| ***C07K 1/22*** | (2006.01) |

(52) U.S. Cl.

CPC .............. *C12N 9/6432* (2013.01); *C07K 1/18* (2013.01); *C07K 1/20* (2013.01); *C07K 1/22* (2013.01)

(58) Field of Classification Search

None

See application file for complete search history.

(56) References Cited

U.S. PATENT DOCUMENTS

| | | | |
|---|---|---|---|
| 5,189,019 A | 2/1993 | Palladino et al. | |
| 5,589,571 A | 12/1996 | King | |
| 10,604,748 B2 * | 3/2020 | Karbarz | A61P 7/04 |
| 2014/0346397 A1 | 11/2014 | Pandey et al. | |
| 2015/0025011 A1 | 1/2015 | Sinha et al. | |

FOREIGN PATENT DOCUMENTS

| | | | |
|---|---|---|---|
| WO | WO-2009/042962 | 4/2009 | |
| WO | WO 2010/117729 | 10/2010 | |
| WO | WO-2013/188587 | 12/2013 | |
| WO | WO-2013188587 A1 * | 12/2013 | C12N 9/6432 |
| WO | WO-2014/116275 | 7/2014 | |
| WO | WO-2016029061 A1 * | 2/2016 | C07K 14/00 |

OTHER PUBLICATIONS

Anonymous, "Prefilter Features PES Nanofleece Material", Biopharm International.com, published Sep. 1, 2013, downloaded Jan. 11, 2019, 4 pages.

Builder et al., "Hydrophobic interaction chromatography principles and methods", 1993, Amersham Biosciences, 104 pages.

Cummings et al., "Protein Chromatography on Hydroxyapatite Columns", Methods Enzymol. 2009, 463:387-404.

International Search Report and Written Opinion for PCT/US2017/038169 dated Sep. 12, 2017, 14 pages.

Justesen et al., "Recombinant chymosin used for exact and complete removal of a prochymosin derived fusion tag releasing intact native target protein", Protein Science, Mar. 16, 2009, vol. 18, pp. 1023-1032.

Lu et al., "A specific antidote for reversal of anticoagulation by direct and indirect inhibitors of coagulation factor Xa", Nature Medicine, Apr. 2013, vol. 19, No. 4, pp. 446-453.

McCue et al., "Manufacturing process used to produce long-acting recombinant factor VIII Fc fusion protein", Biologicals, 2015, 43(4):213-219.

Peixoto et al., "Articles: Bioseparations and Downstream Processing", Biotechnol Prog. 2008, 24(6):1290-1296.

Sinha et al., "Expression, purification, and characterization of inactive human coagulation factor Xa ($Asn^{322}Ala^{419}$)", Protein Expression and Purification, 1992, vol. 3, pp. 518-524.

Supplementary European Search Report for EP Appln. No. 17814267 dated Dec. 10, 2019, 6 pages.

* cited by examiner

*Primary Examiner* — Michael Szperka

(74) *Attorney, Agent, or Firm* — Sheppard Mullin Richter & Hampton LLP

(57) ABSTRACT

The present disclosure provides methods for manufacturing a fXa derivative protein at large scale leading to high yield of highly pure protein product. The method may include adding a detergent to a sample that contains a polynucleotide construct encoding the protein and purifying the protein through a soybean trypsin inhibitor (STI)-based affinity chromatograph, an ion exchange and mixed mode chromatograph and a hydrophobic interaction.

14 Claims, 3 Drawing Sheets

Specification includes a Sequence Listing.

PREPARATION OF FACTOR XA DERIVATIVES

CROSS-REFERENCE TO RELATED PATENT APPLICATIONS

This application is a division of U.S. application Ser. No. 15/626,813, filed Jun. 19, 2017, now U.S. Pat. No. 10,604,748, which claims the benefit of U.S. application Ser. No. 62/351,841, filed Jun. 17, 2016, the contents of each of which are incorporated herein by reference in their entirety.

BACKGROUND

A modified derivative of factor Xa (fXa) protein has been developed that is useful as an antidote to anticoagulants targeting fXa. The derivative is being developed as a universal reversal agent for patients anticoagulated with an oral or injectable factor Xa inhibitor who are in need of having the anticoagulation reversed.

SUMMARY

The present disclosure provides methods for manufacturing a fXa antidote polypeptide in a large scale, leading to high yield of highly pure protein products. In one embodiment, a method is provided for preparing a polypeptide product expressed from a polynucleotide construct comprising the nucleic acid sequence of SEQ ID NO: 7 or a nucleic acid sequence encoding an amino acid sequence having at least 90% sequence identity to the amino acid sequence encoded by SEQ ID NO: 7. The method may include adding a detergent to a sample that contains the polynucleotide construct and purifying the encoded antidote protein through a soybean trypsin inhibitor (STI)-based affinity chromatograph, an ion exchange and mixed mode chromatograph and/or a hydrophobic interaction.

In one embodiment, provided is a method for preparing a polypeptide product expressed from a polynucleotide construct comprising the nucleic acid sequence of SEQ ID NO: 7 or a nucleic acid sequence encoding an amino acid sequence having at least 90% sequence identity to the amino acid sequence encoded by SEQ ID NO: 7, comprising adding a detergent to a sample that contains the polynucleotide construct and a polypeptide product expressed from the polynucleotide construct; loading the sample to a soybean trypsin inhibitor (STI)-based affinity chromatograph and eluting the polypeptide with a first elution buffer to generate a first eluted sample, wherein the loaded sample does not contain an organic solvent; loading the first eluted sample to an ion exchange and mixed mode chromatograph and eluting the polypeptide with a second elution buffer comprising at least 1M of an inorganic salt to generate a second eluted sample; and loading the second eluted sample to a hydrophobic interaction chromatograph and eluting the polypeptide with a third elution buffer comprising at least 2 mM sodium chloride, thereby preparing a purified sample comprising the polypeptide product.

In some embodiments, the detergent comprises Triton X-100 (polyethylene glycol p-(1,1,3,3-tetramethylbutyl)-phenyl ether). In some embodiments, the first elution buffer comprises 0.5M to 2M arginine. In some embodiments, the first elution buffer has a pH of about 5 to 5.4. In some embodiments, the ion exchange and mixed mode chromatograph comprises a ceramic hydroxyapatite type I chromatograph.

In some embodiments, the second elution buffer comprises at least 2M of the inorganic salt. In some embodiments, the inorganic salt is sodium chloride. In some embodiments, the hydrophobic interaction chromatograph comprises an octyl sepharose chromatograph.

In some embodiments, the method further comprises a purification step with an anion exchange chromatograph. In some embodiments, the anion exchange chromatograph comprises a Sartobind™ ion exchange membrane.

In some embodiments, the method further comprises subjecting one or more of the samples to filtration with a nanofleece filter. In some embodiments, the filtration with the nanofleece filter is prior to loading the sample to the STI-based affinity chromatograph.

In some embodiments, the purified sample contains less than about 1% of contaminant proteins not expressed by the polynucleotide construct. In some embodiments, the polypeptide product is expressed in a cell that contains the polynucleotide construct. In some embodiments, the cell is grown in a medium under conditions to produce at least 100 mg of the polypeptide product per liter of medium. In some embodiments, the cell is grown in a medium under conditions to produce at least 200 mg of the polypeptide product per liter of medium. In some embodiments, the purified sample contains more than about 50% of the polypeptide product produced in the medium. In some embodiments, the purified sample contains more than about 100 mg of the polypeptide product from each liter production of the medium.

In some embodiments, the polypeptide product is a two-chain polypeptide comprising a light chain and a heavy chain. In some embodiments, about 20% to 50% of the polypeptide product in the purified sample has a heavy chain consisting of the amino acid sequence of SEQ ID NO: 5. In some embodiments, about 5%-95% of the heavy chain consisting of the amino acid sequence of SEQ ID NO: 5 has two O-linked glycosylations and about 5%-95% of the heavy chain consisting of the amino acid sequence of SEQ ID NO: 5 has one O-linked glycosylation. In some embodiments, about 40-80% of the polypeptide product in the purified sample has a heavy chain consisting of the amino acid sequence of SEQ ID NO: 8. In some embodiments, at least about 90% of the heavy chain consisting of the amino acid sequence of SEQ ID NO: 8 has one O-linked glycosylation. In some embodiments, about 2%-12% of the polypeptide product in the purified sample has a heavy chain consisting of the amino acid sequence of SEQ ID NO: 9. In some embodiments, about 0.1%-1.5% of the polypeptide product in the purified sample has a heavy chain consisting of the amino acid sequence of SEQ ID NO: 10. In some embodiments, about 2%-8% of the polypeptide product in the purified sample has a heavy chain consisting of the amino acid sequence of SEQ ID NO: 11. In some embodiments, about 35%-60% of the polypeptide product in the purified sample has a light chain consisting of the amino acid sequence of SEQ ID NO: 4.

Also provided, in one embodiment, is a polypeptide prepared by a method of any one of the embodiments.

In one embodiment, provided is a pharmaceutical composition comprising a pharmaceutically acceptable carrier and a polypeptide portion of two-chain polypeptides wherein: about 35%-60% of the two-chain polypeptides have a light chain consisting of the amino acid sequence of SEQ ID NO: 4; about 20%-60% of the two-chain polypeptides have a heavy chain consisting of the amino acid sequence of SEQ ID NO: 5; about 40%-60% of the two-chain polypeptides have a heavy chain consisting of the amino acid sequence of SEQ ID NO: 8; and less than 10% of the two-chain polypeptides have a heavy chain consisting of the amino acid sequence of SEQ ID NO: 9.

In some embodiments, less than 5% of the two-chain polypeptides have a heavy chain consisting of the amino acid sequence of SEQ ID NO: 9. In some embodiments, less than 3% of the two-chain polypeptides have a heavy chain consisting of the amino acid sequence of SEQ ID NO: 9. In some embodiments, about 0.1%-1.5% of the two-chain polypeptides have a heavy chain consisting of the amino acid sequence of SEQ ID NO: 10. In some embodiments, about 2%-8% of the two-chain polypeptides have a heavy chain consisting of the amino acid sequence of SEQ ID NO: 11. In some embodiments, about 30%-70% of the heavy chain consisting of the amino acid sequence of SEQ ID NO: 5 has two O-linked glycosylations. In some embodiments, about 30%-70% of the heavy chain consisting of the amino acid sequence of SEQ ID NO: 5 has one O-linked glycosylation. In some embodiments, at least about 90% of the heavy chain consisting of the amino acid sequence of SEQ ID NO: 8 has one O-linked glycosylation.

In some embodiments, the preparation is lyophilized. In some embodiments, the composition further comprises L-arginine HCl or L-arginine acetate. In some embodiments, the composition further comprises sucrose. In some embodiments, the composition further comprises mannitol.

Also provided, in one embodiment, is a method for reversing or inhibiting anticoagulation in a patient undergoing an anticoagulation treatment with a factor Xa inhibitor, comprising administering to the patient a pharmaceutical composition of any one of the embodiments of the present disclosure.

DETAILED DESCRIPTION

Definitions

Figure 1:
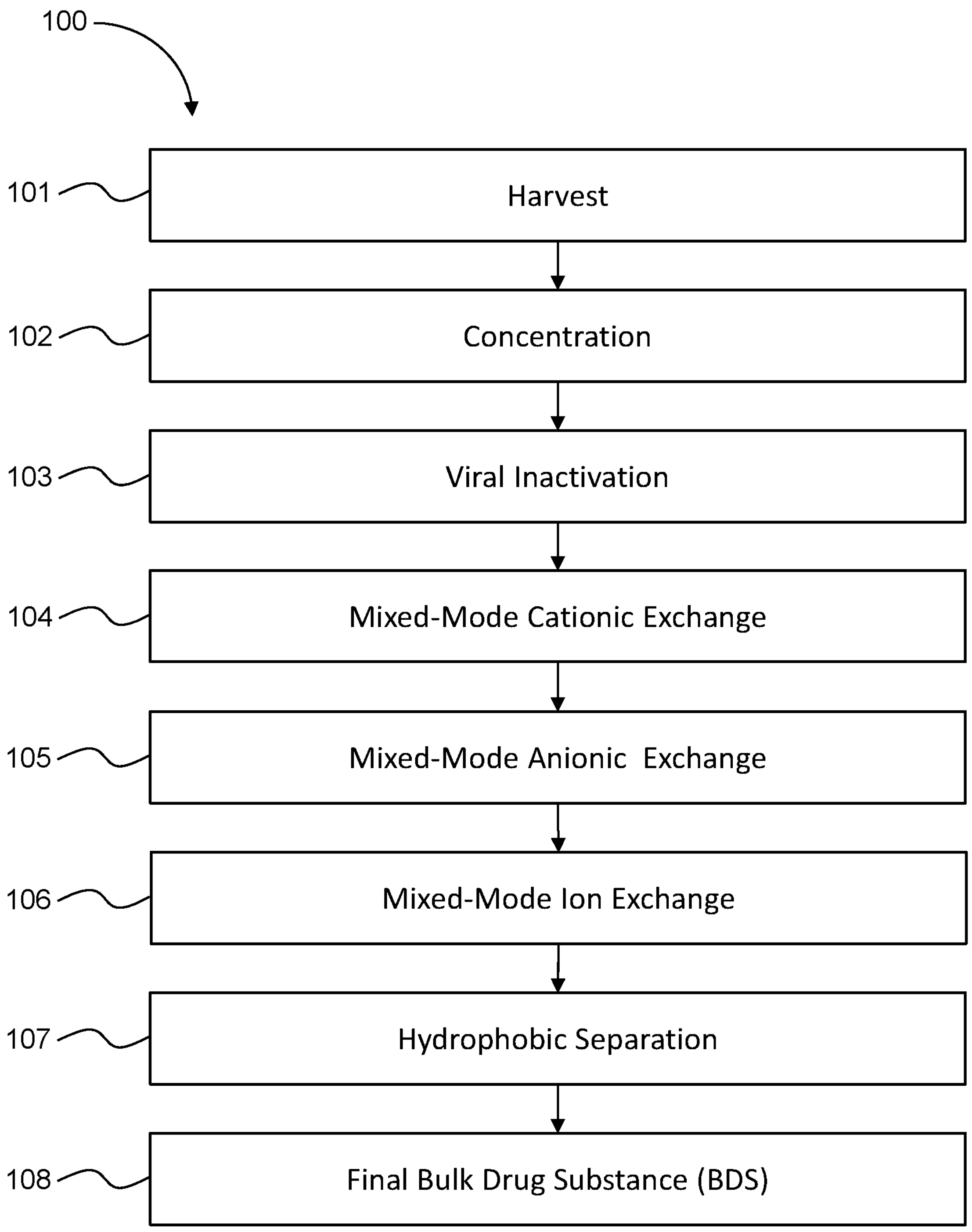
FIG. 1 illustrates a purification process.

The following description sets forth exemplary embodiments of the present technology. It should be recognized, however, that such description is not intended as a limitation on the scope of the present disclosure but is instead provided as a description of exemplary embodiments.

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below.

"Factor Xa" or "fXa" or "fXa protein" is a serine protease in the blood coagulation pathway, which is produced from the inactive factor X (fX, SEQ ID NO. 1, Table 1). The nucleotide sequence coding human factor X ("fX") can be found in GenBank with accession number "NM_000504." Upon catalytic cleavage of the first 52 residues of the heavy chain, fX is activated to fXa. FXa contains a light chain and a heavy chain. The first 45 amino acid residues (residues 1-45 of SEQ ID NO. 1) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 1). Chymotrypsin digestion selectively removes the 1-44 residues resulting in Gla-domainless fXa. The serine protease catalytic domain of fXa locates at the C-terminal heavy chain. The heavy chain of fXa is highly homologous to other serine proteases such as thrombin, trypsin, and activated protein C.

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the procoagulant activity of activating prothrombin. "Active fXa" may be a native fXa or modified fXa that retains procoagulant activity.

As used herein, "fXa antidote", "antidote," or "fXa derivative" refers to a modified fXa protein that does not compete with fXa in assembling into the prothrombinase complex and has reduced or no procoagulant or catalytic activities, and yet binds and/or substantially neutralizes the anticoagulants, such as fXa inhibitors. "Procoagulant activity" of an fXa protein or fXa derivative, in some aspects, refers to the enzymatic activity that the wild-type active fXa polypeptide carries. Examples of fXa derivatives are provided in U.S. Pat. No. 8,153,590, and PCT publications WO2009/042962 and WO2010/056765, and further provided herein, such as SEQ ID NO: 2 and 3 and biological equivalents thereof.

The "enzymatic activity" of an fXa polypeptide or derivatives thereof refers to the polypeptide's ability to catalyze a biochemical reaction with a substrate through direct interaction with the substrate.

SEQ ID NO: 2 contains 3 mutations relative to the wild type fXa. The first mutation is the deletion of 6-39 aa in the Gla-domain of fX. The second mutation is replacing the activation peptide sequence 143-194 aa with —RKR—. This produces a —RKRRKR— (SEQ ID NO: 6) linker connecting the light chain (SEQ ID NO: 4) and the heavy chain (SEQ ID NO: 5). Upon secretion, this linker is cleaved resulting in a two-chain polypeptide, SEQ ID NO: 3 (r-Antidote). The third mutation is mutation of active site residue S379 to an Ala residue. This amino acid substitution corresponds to amino acid 296 and 290 of SEQ ID NOS: 1 and 3, respectively.

An example antidote is the "r-Antidote" which refers to a processed two-chain polypeptide processing product of SEQ ID NO: 2, after cleavage of the linker. This is represented by SEQ ID NO: 3. The r-antidote is disclosed in, e.g., U.S. Pat. No. 8,153,590, the content of which is incorporated to the present disclosure by reference. The r-Antidote includes a light chain (SEQ ID NO. 4) and a heavy chain (SEQ ID NO. 5) connected with a single disulfide bond between Cysteine 98 (Cys98) of the light chain and Cysteine 108 (Cys108) of the heavy chain. Like the wild-type fXa, in certain production batches, the r-Antidote undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

TABLE 1

| Polypeptide Sequence of Inactive Human Factor X (SEQ ID NO: 1) | | | | | | |
|---|---|---|---|---|---|---|
| 1 | ANSFLEEMKK | GHLERECMEE | TCSYEEAREV | FEDSDKTNEF | WNKYKDGDQC | ETSPCQNQGK |
| 61 | CKDGLGEYTC | TCLEGFEGKN | CELFTRKLCS | LDNGDCDQFC | HEEQNSVVCS | CARGYTLADN |
| 121 | GKACIPTGPY | PCGKQTLERR | KRSVAQATSS | SGEAPDSITW | KPYDAADLDP | TENPFDLLDF |
| 181 | NQTQPERGDN | NLTRIVGGQE | CKDGECPWQA | LLINEENEGF | CGGTILSEFY | ILTAAHCLYQ |
| 241 | AKRFKVRVGD | RNTEQEEGGE | AVHEVEVVIK | HNRFTKETYD | FDIAVLRLKT | PITFRMNVAP |
| 301 | ACLPERDWAE | STLMTQKTGI | VSGFGRTHEK | GRQSTRLKML | EVPYVDRNSC | KLSSSFIITQ |
| 361 | NMFCAGYDTK | QEDACQGDSG | GPHVTRFKDT | YFVTGIVSWG | EGCARKGKYG | IYTKVTAFLK |
| 421 | WIDRSMKTRG | LPKAKSHAPE | VITSSPLK | | | |

TABLE 2

| Polypeptide Sequence of the r-Antidote precursor prior to removal of the -RKRRKR- (SEQ ID NO. 6) linker (SEQ ID NO: 2) | | | | | | |
|---|---|---|---|---|---|---|
| Light Chain (SEQ ID NO: 4) | | | | | | |
| 1 | ANSFL | | | F | WNKYKDGDQC | ETSPCQNQGK |
| 61 | CKDGLGEYTC | TCLEGFEGKN | CELFTRKLCS | LDNGDCDQFC | HEEQNSVVCS | CARGYTLADN |
| 121 | GKACIPTGPY | PCGKQTLER | | | | |
| Linker (SEQ ID NO: 6) | | | | | | |
| | RKRRKR | | | | | |
| Heavy Chain (SEQ ID NO: 5) | | | | | | |
| 181 | | IVGGQE | CKDGECPWQA | LLINEENEGF | CGGTILSEFY | ILTAAHCLYQ |
| 241 | AKRFKVRVGD | RNTEQEEGGE | AVHEVEVVIK | HNRFTKETYD | FDIAVLRLKT | PITFRMNVAP |
| 301 | ACLPERDWAE | STLMTQKTGI | VSGFGRTHEK | GRQSTRLKML | EVPYVDRNSC | KLSSSFIITQ |
| 361 | NMFCAGYDTK | QEDACQGD**A**G | GPHVTRFKDT | YFVTGIVSWG | EGCARKGKYG | IYTKVTAFLK |
| 421 | WIDRSMKTRG | LPKAKSHAPE | VITSSPLK | | | |

TABLE 3

| Polypeptide Sequence of a Human Factor Xa triple mutant after removal of the -RKRRKR- (SEQ ID NO. 6) linker (SEQ ID NO: 3) | | | | | | |
|---|---|---|---|---|---|---|
| Light Chain (SEQ ID NO: 4) | | | | | | |
| 1 | ANSFL | | | F | WNKYKDGDQC | ETSPCQNQGK |
| 61 | CKDGLGEYTC | TCLEGFEGKN | CELFTRKLCS | LDNGDCDQFC | HEEQNSVVCS | CARGYTLADN |
| 121 | GKACIPTGPY | PCGKQTLER | | | | |

TABLE 3-continued

| Polypeptide Sequence of a Human Factor Xa triple mutant after removal of the -RKRRKR- (SEQ ID NO. 6) linker (SEQ ID NO: 3) |
|---|
| Heavy Chain (SEQ ID NO: 5) |
| 181 IVGGQE CKDGECPWQA LLINEENEGF CGGTILSEFY ILTAAHCLYQ |
| 241 AKRFKVRVGD RNTEQEEGGE AVHEVEVVIK HNRFTKETYD FDIAVLRLKT PITFRMNVAP |
| 301 ACLPERDWAE STLMTQKTGI VSGFGRTHEK GRQSTRLKML EVPYVDRNSC KLSSSFIITQ |
| 361 NMFCAGYDTK QEDACQGDAG GPHVTRFKDT YFVTGIVSWG EGCARKGKYG IYTKVTAFLK |
| 421 WIDRSMKTRG LPKAKSHAPE VITSSPLK |

TABLE 4

| Nucleotide sequence encoding the r-Antidote precursor (SEQ ID NO: 7) |
|---|
| ATGGGGCGCC CACTGCACCT CGTCCTGCTC AGTGCCTCCC |
| TGGCTGGCCT CCTGCTGCTC GGGGAAAGTC TGTTCATCCG |
| CAGGGAGCAG GCCAACAACA TCCTGGCGAG GGTCACGAGG |
| GCCAATTCCT TTCTTTTCTG GAATAAATAC AAAGATGGCG |
| ACCAGTGTGA GACCAGTCCT TGCCAGAACC AGGGCAAATG |
| TAAAGACGGC CTCGGGGAAT ACACCTGCAC CTGTTTAGAA |
| GGATTCGAAG GCAAAAACTG TGAATTATTC ACACGGAAGC |
| TCTGCAGCCT GGACAACGGG GACTGTGACC AGTTCTGCCA |
| CGAGGAACAG AACTCTGTGG TGTGCTCCTG CGCCCGCGGG |
| TACACCCTGG CTGACAACGG CAAGGCCTGC ATTCCCACAG |
| GGCCCTACCC CTGTGGGAAA CAGACCCTGG AACGCAGGAA |
| GAGGAGGAAG AGGATCGTGG GAGGCCAGGA ATGCAAGGAC |
| GGGGAGTGTC CCTGGCAGGC CCTGCTCATC AATGAGGAAA |
| ACGAGGGTTT CTGTGGTGGA ACCATTCTGA GCGAGTTCTA |
| CATCCTAACG GCAGCCCACT GTCTCTACCA AGCCAAGAGA |
| TTCAAGGTGA GGGTAGGGGA CCGGAACACG GAGCAGGAGG |
| AGGGCGGTGA GGCGGTGCAC GAGGTGGAGG TGGTCATCAA |
| GCACAACCGG TTCACAAAGG AGACCTATGA CTTCGACATC |
| GCCGTGCTCC GGCTCAAGAC CCCCATCACC TTCCGCATGA |
| ACGTGGCGCC TGCCTGCCTC CCCGAGCGTG ACTGGGCCGA |
| GTCCACGCTG ATGACGCAGA AGACGGGGAT TGTGAGCGGC |
| TTCGGGCGCA CCCACGAGAA GGGCCGGCAG TCCACCAGGC |
| TCAAGATGCT GGAGGTGCCC TACGTGGACC GCAACAGCTG |
| CAAGCTGTCC AGCAGCTTCA TCATCACCCA GAACATGTTC |
| TGTGCCGGCT ACGACACCAA GCAGGAGGAT GCCTGCCAGG |
| GGGACGCAGG GGGCCCGCAC GTCACCCGCT TCAAGGACAC |
| CTACTTCGTG ACAGGCATCG TCAGCTGGGG AGAGGGCTGT |
| GCCCGTAAGG GGAAGTACGG GATCTACACC AAGGTCACCG |
| CCTTCCTCAA GTGGATCGAC AGGTCCATGA AAACCAGGGG |

TABLE 4-continued

| Nucleotide sequence encoding the r-Antidote precursor (SEQ ID NO: 7) |
|---|
| CTTGCCCAAG GCCAAGAGCC ATGCCCCGGA GGTCATAACG |
| TCCTCTCCAT TAAAGTGA |

Other example antidotes can be biological equivalents of the r-Antidote (or their precursors, represented by SEQ ID NO: 2), or alternatively polypeptides having certain sequence identity to SEQ ID NO: 3. In one aspect, such biological equivalents retain the structural characteristics of SEQ ID NO: 3, that is, a modified active site and a deleted or modified Gla domain. In another aspect, such biological equivalents retain the functional features of SEQ ID NO: 3, that is, not competing with fXa in assembling into the prothrombinase complex and having reduced or no procoagulant (e.g., enzymatic or catalytic) activities.

The term "active site" refers to the part of an enzyme or antibody where a chemical reaction occurs. A "modified active site" is an active site that has been modified structurally to provide the active site with increased or decreased chemical reactivity or specificity. Examples of active sites include, but are not limited to, the catalytic domain of human factor X comprising the 235-488 amino acid residues, and the catalytic domain of human factor Xa comprising the 195-448 amino acid residues. Examples of modified active site include, but are not limited to, the catalytic domain of human factor Xa comprising 195-448 amino acid residues in SEQ ID NO: 1 with at least one amino acid substitution at position Arg306, Glu310, Arg347, Lys351, Lys414, or Arg424.

Preparation of Antidotes

The experimental examples (Examples 1 and 2) demonstrated the development of culturing and purification methods for preparing fXa antidotes. The cultured cells include a polynucleotide construct comprising the nucleic acid sequence of SEQ ID NO: 7 or a nucleic acid sequence encoding an amino acid sequence having at least 90% sequence identity (or at least 91%, 92%, 93%, 94%, 95%, 96%, 97%, 98% or 99% sequence identity) to the amino acid sequence encoded by SEQ ID NO: 7. The cell is typically a Chinese hamster ovary (CHO) cell.

One of the purification methods is illustrated in FIG. 1. After the cells are harvested (step 101) and clarified using a depth filter to remove high molecule weight (HWM) impurity, the sample is concentrated (e.g., by about 10 fold) (step 102). The concentrating step can use regenerated cellulose, without limitation. At step 103, viral inactivation (e.g., with a detergent/solvent; such as 1% Triton X-100, 0.3% Tributyl Phosphate (final concentration)) can be carried out to inactivate enveloped viruses in the cell culture. Following removal of the viruses, steps 104 (mixed-mode cationic exchange), 105 (mixed-mode anionic exchange) and 106 (mixed-mode ion exchange) are carried out to remove host cell proteins and DNA and capture the antidote. At step 107, a hydrophobic interaction resin can be used to further remove remaining host cell proteins. Optionally, after these purification steps, a final virus removal filtration step can be used to remove any remaining viruses.

Figure 2:
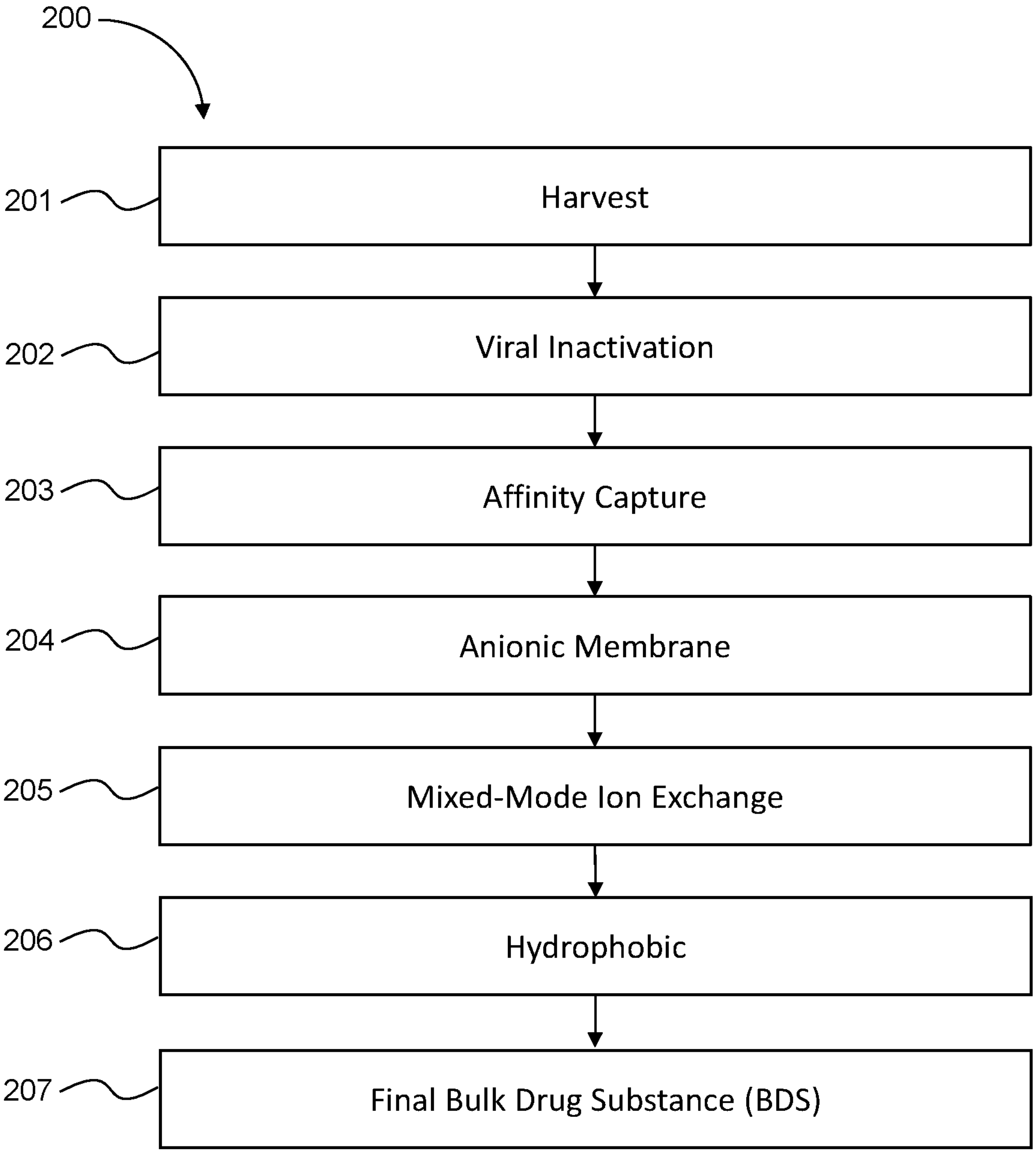
FIG. 2 illustrates another purification process.

In another embodiment, the purification process is as illustrated in FIG. 2 and demonstrated in Example 2. In some embodiments, the method includes adding a detergent to a sample that contains the polynucleotide construct (e.g., SEQ ID NO: 7) and a polypeptide product expressed from the polynucleotide construct (e.g., SEQ ID NO: 3). In some embodiments, the detergent includes Triton X-100. In some embodiments, no solvent is used to treat the sample before the sample is subjected to the subsequent affinity purification. In some embodiments, no organic solvent is used to treat the sample before the sample is subjected to the subsequent affinity purification. In some embodiments, tributyl phosphate is not added to the sample before the sample is subjected to the subsequent affinity purification.

In some embodiment, the sample is then loaded to a soybean trypsin inhibitor (STI)-based affinity chromatograph and eluted with an elution buffer to generate an eluted sample. In some embodiments, the loaded sample has not been treated with an organic solvent or does not contain an organic solvent.

"STI" or "Soybean Trypsin Inhibitor," refers to trypsin inhibitors isolated from soybeans, or their biological equivalents. Trypsin inhibitors are about 20 kDa in size and reduce trypsin (a proteolytic enzyme) as well as plasma kallikrein, factor Xa and plasmin activity. STI are commercially available from vendors such as Life Technologies (Grand Island, N.Y.). An example of STI is KTI3 Kunitz trypsin inhibitor, from *Glycine max* (soybean), having a GenBank accession number NP_001238611.

The STI can be immobilized on a solid support resin for the purification of certain proteins. In addition to Soybean Trypsin Inhibitor, other trypsin inhibitor proteins such as those isolated from serum, lima beans, bovine pancreas, or ovomucoid, or the modified forms thereof can also be used. It is also contemplated that certain protease inhibitors, in particular serine protease inhibitors, can be used to prepare affinity resin for the purpose of purifying the antidote. The antidote may then be eluted with a buffer that contains arginine. In some embodiments, the elution buffer includes at least 0.2M, 0.5M, 0.6M, 0.7M, 0.8M, 0.9M, 1M, 1.1M, 1.2M, 1.3M, 1.4M, 1.5M, or 2M arginine. In some embodiments, the elution buffer includes about 0.5M to 2M arginine, or about 0.7M to 1.5M arginine, or 0.8M to 1.2M arginine. In some embodiment, the elution buffer has pH of about 4.5 to 6, or from 4.6 to 5.6, or from 4.7 to 5.5, or from 4.8 to 5.4, or from 5 to 5.4, or from 5.1 to 5.3 or about 5.2. In one embodiment, the elution buffer includes 25 mM sodium acetate 1.0 M arginine at pH 5.2.

In some embodiments, the sample is then loaded to an ion exchange and mixed mode chromatograph. Non-limiting examples of ion exchange and mixed mode chromatograph include a ceramic hydroxyapatite type I chromatograph. The sample may then be eluted with an elution buffer that includes an inorganic salt. In some embodiments, the inorganic salt is sodium chloride or potassium chloride. In some embodiments, the concentration of the salt in the elution buffer is at least 0.5M, 1M, 1.5M, 2M, 2.5M or 3M.

In some embodiments, the elution entails the use of a gradient generated between an equilibration buffer and an elution buffer. The equilibration buffer, in some embodiments, includes a lower concentration of the salt, e.g., less than 0.2M, less than 0.1M, less than 50 mM, less than 20 mM, less than 10 mM. In some embodiments, the gradient includes at least 5 fold, or 10 fold, or 20 fold, or 50 fold, or 100 fold increase of the salt concentration. In some embodiments, the equilibration buffer includes 50 mM MES (2-(N-morpholino)ethanesulfonic acid), 5 mM Sodium Phosphate, at pH 7.0. In some embodiments, the elution buffer includes 50 mM MES, 5 mM Sodium Phosphate, 2M Sodium Chloride pH 7.0. In some embodiments, the gradient starts with about 90% equilibration buffer and ends with about 90% elution buffer.

In some embodiments, the sample is further loaded to hydrophobic interaction chromatograph. In some embodiments, the hydrophobic interaction chromatograph comprises an octyl sepharose chromatograph. In some embodiments, the sample is eluted with an elution buffer that includes at least 2 mM sodium chloride, or alternatively at least 1M, 1.5M, 2.5M, 3M, 4M or 5M sodium chloride.

In some embodiments, one of the intermediate samples described above is further subjected to a purification step with an anion exchange chromatograph. In some embodiments, the anion exchange chromatograph comprises a Sartobind™ ion exchange membrane. In some embodiments, the anion exchange chromatograph is applied after the affinity chromatograph.

In some embodiments, one of the intermediate samples described above is further subjected to filtration with a nanofleece filter. In some embodiments, the nanofleece filtration is applied prior to loading the sample to the STI-based affinity chromatograph.

In some embodiments, the purified sample contains less than about 1% of contaminant proteins not expressed by the polynucleotide construct, such as host cell proteins or STI that is released from the affinity resin/column.

The purification process of any of the above embodiments may be able to recover at least about 50% (or at least about 40%, 45%, 55%, 60%, 65%, 70%, 75%, 80% or 85%) of the antidote protein expressed in the cell culture. In some embodiments, the cell is grown in a medium under conditions to produce at least 100 mg of the polypeptide product per liter of medium. In some embodiments, the cell is grown in a medium under conditions to produce at least 120 mg (or at least 210 mg, 220 mg, 230 mg, 240 mg, 250 mg, 270 mg, 280 mg, 290 mg, 300 mg, 310 mg, 320 mg, 330 mg, 340 mg, or 350 mg) of the polypeptide product per liter of medium. In some embodiments, the purified sample contains more than about 50 mg (or at least 55 mg, 60 mg, 70 mg, 80 mg, 90 mg, 100 mg, 110 mg, 120 mg, 130 mg, 140 mg, 150 mg, 160 mg, 170 mg, 180 mg, 190 mg or 200 mg) of the polypeptide product from each liter production of the medium.

Antidote Isomers in the Purified Product

The purified antidote product, from a method of any of the embodiments of the present disclosure, is supposed to include a light chain and a heavy chain. The culturing and purification processes, however, may introduce variations to the actual protein.

As demonstrated in Example 3, about 20% to 50% of the polypeptide product in the purified sample has an intact heavy chain (SEQ ID NO: 5). Among these that have an intact heavy chain, about 5%-95% of the heavy chain has two O-linked glycosylations and about 5%-95% of the heavy chain has one O-linked glycosylation.

In some embodiments, at least about 20%, 25%, 30%, 35%, 40% or 45% polypeptide product in the purified sample has an intact heavy chain. In some embodiments, no more than about 40%, 45%, 50%, 55%, 60%, 65%, 70%, 75%, or 80% polypeptide product in the purified sample has an intact heavy chain.

In some embodiments, about 40-80% of the polypeptide product in the purified sample has a heavy chain that has a deletion of the C-terminal lysine (SEQ ID NO: 8). In some embodiments, SEQ ID NO: 8 constitutes at least about 20%, 25%, 30%, 35%, 40%, 45% or 50% in the purified sample. In some embodiments, SEQ ID NO: 8 constitutes no more than about 45%, 50%, 55%, 60%, 65%, 70%, 75%, 80%, 85%, or 90% in the purified sample. In some embodiments, at least about 90% of the heavy chain of SEQ ID NO: 8 has one O-linked glycosylation.

In some embodiments, about 2%-12% of the polypeptide product in the purified sample has a heavy chain that has a deletion of 13 C-terminal amino acid residues (SEQ ID NO: 9). In some embodiments, SEQ ID NO: 9 constitutes at least about 0.5%, 1%, 1.5%, 2%, 2.5%, 3% or 5% in the purified sample. In some embodiments, SEQ ID NO: 9 constitutes no more than about 2%, 3%, 4%, 5%, 7%, 10%, 15%, 17% or 20% in the purified sample.

In some embodiments, about 0.1%-1.5% of the polypeptide product in the purified sample has a heavy chain that has a deletion of 14 C-terminal amino acid residues (SEQ ID NO: 10). In some embodiments, SEQ ID NO: 10 constitutes at least about 0.05%, 0.1%, 0.15%, 0.2%, 0.25%, 0.3% or 0.5% in the purified sample. In some embodiments, SEQ ID NO: 10 constitutes no more than about 0.5%, 0.6%, 0.7%, 0.8%, 0.9%, 1%, 1.5%, 2%, 2.5% or 3% in the purified sample.

In some embodiments, about 2%-8% of the polypeptide product in the purified sample has a heavy chain that has a deletion of 15 C-terminal amino acid residues (SEQ ID NO: 11). In some embodiments, SEQ ID NO: 11 constitutes at least about 0.5%, 1%, 1.5%, 2%, 2.5%, 3% or 5% in the purified sample. In some embodiments, SEQ ID NO: 11 constitutes no more than about 5%, 6%, 7%, 8%, 9% or 10% in the purified sample.

Example 3 also shows that about 35%-60% of the polypeptide product in the purified sample has an intact light chain (SEQ ID NO: 4) while some others may be modified or truncated. In some embodiments, the amount of intact light chain in the total number of light chain is at least about 20%, 25%, 30%, 35%, 40%, 45% or 50%. In some embodiments, the amount of intact light chain in the total number of light chain is no more than about 45%, 50%, 55%, 60%, 65%, 70%, 80% or 90%.

In some embodiments, the present disclosure provides a pharmaceutical preparation comprising a pharmaceutically acceptable carrier and a polypeptide portion of two-chain polypeptides wherein about 35%-60% of the two-chain polypeptides have a light chain consisting of the amino acid sequence of SEQ ID NO: 4. In some embodiments, about 20%-50% of the two-chain polypeptides have a heavy chain consisting of the amino acid sequence of SEQ ID NO: 5. In some embodiments, about 40%-80% of the two-chain polypeptides have a heavy chain consisting of the amino acid sequence of SEQ ID NO: 8. In some embodiments, less than about 10%, 9%, 8%, 7%, 6%, 5%, 4% or 3% of the two-chain polypeptides have a heavy chain consisting of the amino acid sequence of SEQ ID NO: 9. In some embodiments, about 0.1%-1.5% of the two-chain polypeptides have a heavy chain consists of the amino acid sequence of SEQ ID NO: 10. In some embodiments, about 2%-8% of the two-chain polypeptides have a heavy chain consists of the amino acid sequence of SEQ ID NO: 11.

In some embodiments, about 5%-95% of the heavy chain consisting of the amino acid sequence of SEQ ID NO: 5 has two O-linked glycosylations. In some embodiments, about 5%-95% of the heavy chain consisting of the amino acid sequence of SEQ ID NO: 5 has one O-linked glycosylation. In some embodiments, at least about 90% of the heavy chain consisting of the amino acid sequence of SEQ ID NO: 8 has one O-linked glycosylation.

Formulations, Methods and Dosages

Formulations prepared with purified antidote protein products are also provided. In some embodiments, an aqueous formulation is provided that is suitable for lyophilization. In one embodiment, the formulation includes an antidote along with a solubilizing agent, a stabilizing agent (or stabilizer), and a crystalline agent. The formulation can further include a surfactant and/or a buffer. In some aspects, the presence of each of these agents prevents the antidote from collapsing during lyophilization, for instance, when the freeze-dry temperature is higher than −40° C., −30° C., −20° C., −10° C., 0° C., 5° C., 10° C., or 15° C., as high as 20° C. or 25° C.

A "crystalline component" refers to a molecule that forms a crystalline matrix in a formulation that includes a polypeptide, during a freeze drying process. Non-limiting examples of crystalline components include mannitol and glycine.

In some aspects, the crystalline component is mannitol (e.g., crystalline mannitol). In one aspect, the concentration of the crystalline component in the aqueous formulation is at least 1% (w/v). In one aspect, the concentration of the crystalline component in the aqueous formulation is at least 1.5%, 2%, 2.5%, 3%, 3.5% or 4% (w/v). In one aspect, the concentration of the crystalline component in the aqueous formulation is not higher than 8%, or alternatively not higher than 7%, 6.5%, 6%, 5.5%, 5%, 4.5% or 4% (w/v). In one aspect, the concentration of the crystalline component in the aqueous formulation is from about 1% to about 8%, or from about 2% to about 6%, or from about 3% to about 5.5%, or from about 4.5% to about 5.5%, or from about 4.6% to about 5.4%, or from about 4.7% to about 5.3%, or from about 4.8% to about 5.2%, or from about 4.9% to about 5.1%, or at about 4%, 4.5%, or 5% (w/v).

In some aspects, a solubilizing agent is included in the aqueous formulation. The term "solubilizing agent" refers to salts, ions, carbohydrates, complexation agent, polymers and other compounds which, when present in solution, increase the solubility of another molecule (e.g., an active ingredient) in the solution. Non-limiting examples of solubilizing agents include arginine and citrate. In one aspect, the solubilizing agent is arginine. In one aspect, the solubilizing agent is citrate.

The presence of the solubilizing agent may be useful in keeping the fXa polypeptide soluble and stable in the formulation. In some aspects, the concentration of the solubilizing agent (e.g., arginine) is at least 10 mM, or alternatively at least 20 mM, 25 mM, 30 mM, 36 mM, or 40 mM. In some aspects, the concentration of the solubilizing agent (e.g., arginine) is not higher than 100 mM, 96 mM, 90 mM, 80 mM, 70 mM, 60 mM or 50 mM. In some aspects, the concentration of the solubilizing agent is from about 10 mM or 20 mM to about 60 mM, from about 10 mM or 20 mM to about 55 mM, from about 35 mM to about 55 mM, from about 40 mM to about 50 mM, from about 41 mM to about 49 mM, from about 42 mM to about 48 mM, from about 43 mM to about 47 mM, from about 44 mM to about 46 mM, or at about 40 mM, 45 mM or 50 mM. It is noted that as used herein, the term arginine refers to the amino acid as well as the salts (e.g., arginine HCl) thereof. Arginine has a molecular weight of about 174.2 Dalton and arginine HCl (e.g., L-arginine HCl, L-arginine acetate) has a molecular weight of about 210.7 Dalton.

In one embodiment, the solubilizing agent is citrate or a salt thereof. The salt of citrate is sodium citrate. In one aspect, the citrate comprises a concentration from about 1.0 mM to about 200.0 mM. In a further aspect, the concentration of the citrate is about 25 mM. In another aspect, the concentration of the citrate is about 50 mM. In further embodiment, the concentration of the citrate is about 5 mM, 10 mM, or 20 mM. In another embodiment, the citrate comprises a concentration from about 0.05 M to about 0.2 M.

In some aspects, a stabilizer is included in the aqueous formulation. The term "stabilizer" denotes a pharmaceutical acceptable excipient, which protects the active ingredient (e.g., the fXa derivative polypeptides) and/or the formulation from chemical and/or physical degradation during manufacturing, storage and application. Examples of stabilizers may be include sucrose, arginine, citrate, mannitol, trehalose, glycine, sodium chloride, dextran and glucose. In one aspect, the stabilizer is sucrose.

In one aspect, the concentration of the stabilizer in the aqueous formulation (e.g., sucrose) is at least about 0.5% (w/v). In one aspect, the concentration of the stabilizer in the aqueous formulation (e.g., sucrose) is at least about 0.6%, 0.7%, 0.8%, 0.9%, 1%, 1.1%, 1.2%, 1.3%, 1.4%, 1.5%, 1.6%, 1.7%, 1.8%, 1.9% or 2% (w/v). In one aspect, the concentration of the stabilizer in the aqueous formulation (e.g., sucrose) is not greater than about 5%, 4.5%, 4%, 3.5%, 3%, 2.5% or 2% (w/v). In one aspect, the concentration of the stabilizer in the aqueous formulation (e.g., sucrose) is from about 1% to about 5%, or from about 1% to about 4%, or from about 1% to about 3%, or from about 1.5% to about 2.5%, or from about 1.6% to about 2.4%, or from about 1.7% to about 2.3%, or from about 1.7% to about 2.2%, or from about 1.9% to about 2.1%, or at about 1%, 1.5%, 2%, 2.5% or 3% (w/v).

In some aspects, the aqueous formulation can further include a surfactant, a buffer, a tonicity agent, a cryoprotectant, a surfactant, a lyoprotectant, a preservative or combinations thereof.

In some aspects, the aqueous formulation has a pH that is 6 or higher, or 6.5 or higher, or 7 or higher, or 7.5 or higher. In some aspects, the pH is not higher than 9, 8.5, or 8. In some aspects, the pH is between 6 and 9, between 6.5 and 8.5, between 7 and 8.5, between 7.5 and 8.2, between 7.6 and 8.1, between 7.7 and 7.9, or at about 7.5, 7.6, 7.7, 7.8, 7.9 or 8.

In one aspect, the aqueous formulation includes about 45 mM arginine, about 2% sucrose (w/v), about 5% mannitol (w/v) and about 10 mg/mL of a two-chain r-Antidote, wherein the formulation has a pH of about 7.8. In one aspect, the aqueous formulation includes about 45 mM arginine, about 2% sucrose (w/v), about 5% mannitol (w/v) and about 20 mg/mL of a two-chain r-Antidote, wherein the formulation has a pH of about 7.8. In one aspect, the aqueous formulation includes about 45 mM arginine, about 2% sucrose (w/v), about 5% mannitol (w/v) and about 40 mg/mL of a two-chain r-Antidote, wherein the formulation has a pH of about 7.8. In one aspect, the aqueous formulation further includes 0.01%-0.02% (w/v) Polysorbate 80 and a buffer.

In some aspects, also provided are lyophilized compositions prepared by lyophilizing the aqueous formulation of the present disclosure. Based on the concentrations of each agent in the aqueous formulation, the relative content of the agent in the lyophilized composition can readily be determined.

In one aspect, the lyophilized composition includes at least 5%, or alternatively at least 10%, 15%, 20%, 25%, 30%, or 35% (w/w) of the fXa antidote. Then, among the other main ingredients, for instance, there can be a weight ratio for L-arginine HCl:sucrose:mannitol in the range of (0.5-1.4):(1-3):(2-6). In some aspects, the weight ratio of L-arginine HCl:sucrose:mannitol is in the range of (0.9-1):(1.5-2.5):(4.5-5.5), or (0.91-0.99):(1.6-2.4):(4.6-5.4), or (0.92-0.98):(1.7-2.3):(4.7-5.3), (0.93-0.97):(1.8-2.2):(4.8-5.2), or (0.94-0.96):(1.9-2.1):(4.9-5.1). In some aspects, the lyophilized composition further includes a surfactant and/or the solid portion of a buffer.

The present disclosure also relates to therapeutic methods of treating, preventing or reducing bleeding in a subject undergoing anticoagulant therapy with a fXa inhibitor comprising administering to a subject an effective amount of the lyophilized formulation upon being dissolved in a suitable solvent. It is contemplated that the antidotes or derivatives of the present disclosure may be short-duration drugs to be used in elective or emergency situations, which can safely and specifically neutralize a fXa inhibitor's conventional anticoagulant properties without causing deleterious hemodynamic side-effects or exacerbation of the proliferative vascular response to injury.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but may have not yet been diagnosed as having it, e.g., prevent bleeding in a patient with anticoagulant overdose; (b) inhibiting a disorder, i.e., arresting its development, e.g., inhibiting bleeding; or (c) relieving or ameliorating the disorder, e.g., reducing bleeding.

As used herein, to "treat" further includes systemic amelioration of the symptoms associated with the pathology and/or a delay in onset of symptoms. Clinical and subclinical evidence of "treatment" will vary with the pathology, the individual and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

The agents and compositions of the present disclosure can be used in the manufacture of medicaments and for the treatment of humans and other animals by administration in accordance with conventional procedures, such as an active ingredient in pharmaceutical compositions.

An agent of the present disclosure can be administered for therapy by any suitable route, specifically by parental (including subcutaneous, intramuscular, intravenous and intradermal) administration. It will also be appreciated that the preferred route will vary with the condition and age of the recipient, and the disease being treated.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

"Anticoagulant agents" or "anticoagulants" are agents that inhibit blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Orgaran®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol. In one embodiment, the anticoagulant is an inhibitor of factor Xa. In one embodiment, the anticoagulant is betrixaban.

"Anticoagulant therapy" refers to a therapeutic regime that is administered to a patient to prevent undesired blood clots or thrombosis. An anticoagulant therapy comprises administering one or a combination of two or more anticoagulant agents or other agents at a dosage and schedule suitable for treating or preventing the undesired blood clots or thrombosis in the patient.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo.

"Direct factor Xa inhibitors" bind to the fXa directly and non-limiting examples include NAP-5, rNAPc2, tissue factor pathway inhibitor (TFPI), DX-DX-9065a (as described in, e.g., Herbert, J. M., et al, *J Pharmacol Exp Ther.* 1996 276(3):1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106(11), Abstract 1865), apixaban, rivaroxaban, TAK-442, PD-348292 (as described in, e.g., Pipeline Insight: Antithrombotics—Reaching the Untreated Prophylaxis Market, 2007), otamixaban, edoxaban (as described in, e.g., Hylek E M, Curr Opin Invest Drugs 2007 8(9):778-783), LY517717 (as described in, e.g., Agnelli, G., et al, *J. Thromb. Haemost.* 2007 5(4):746-53), GSK913893, razaxaban, betrixaban or a pharmaceutically acceptable salt thereof, and combinations thereof. In a particular aspect, the direct factor Xa inhibitor is rivaroxaban. In some aspects, a direct fXa inhibitor is a small molecule chemical compound.

"Indirect factor Xa inhibitors" inhibition of the fXa activity is mediated by one or more other factors. Non-limiting examples of indirect factor Xa inhibitors include fondaparinux, idraparinux, biotinylated idraparinux, enoxaparin, fragmin, tinzaparin, low molecular weight heparin ("LMWH"), and combinations thereof. In a particular aspect, the indirect factor Xa inhibitor is enoxaparin.

In one embodiment, the factor Xa inhibitor is selected from betrixaban, rivaroxaban, LMWH, DX-9065a, YM-60828, YM-150, PD-348292, otamixaban, edoxaban, LY517717, GSK913893, razaxaban, apixaban, and combinations thereof.

The term "betrixaban" refers to the compound "[2-({4-[(dimethylamino)iminomethyl]phenyl}carbonylamino)-5-methoxyphenyl]-N-(5-chloro(2-pyridyl))carboxamide" or pharmaceutically acceptable salts thereof. Betrixaban is described in U.S. Pat. Nos. 6,376,515, 6,835,739 and 7,598,276, the contents of which are incorporated herein by reference. Betrixaban is known to be a specific inhibitor of factor Xa.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo.

"An effective amount" refers to the amount of derivative sufficient to induce a desired biological and/or therapeutic result. That result can be alleviation of the signs, symptoms, or causes of a disease, or any other desired alteration of a biological system. In the present disclosure, the result will typically involve one or more of the following: neutralization of a fXa inhibitor that has been administered to a patient, reversal of the anticoagulant activity of the fXa inhibitor, removal of the fXa inhibitor from the plasma, restoration of hemostasis, and reduction or cessation of bleeding. The effective amount will vary depending upon the specific antidote agent used, the specific fXa inhibitor the subject has been administered, the dosing regimen of the fXa inhibitor, timing of administration of the antidote, the subject and disease condition being treated, the weight and age of the subject, the severity of the disease condition, the manner of administration and the like, all of which can be determined readily by one of ordinary skill in the art.

In certain aspects, the solution is administered to deliver an amount of the fXa antidote from about 10 milligrams (mg) to about 2 grams (g). Other amounts of the r-antidote used include from about 100 mg to about 1.5 g; from about 200 mg to about 1 g; and from about 400 mg to about 900 mg. In some aspects, the amount of the r-antidote used is about 400 mg or 960 mg. In some aspects, the amount of the r-antidote used is from about 10 mg to about 100 mg; from about 15 mg to about 95 mg; and from about 20 mg to about 80 mg.

The formulation when administered neutralizes the factor Xa inhibitor by at least about 20%, or by at least about 50%, or by at least about 75%, or by at least about 90%, or by at least about 95%.

One can determine if the method, i.e., inhibition or reversal of a factor Xa inhibitor is achieved, by a number of in vitro assays, such as thrombin generation assay, and clinical clotting assays such as aPTT, PT and ACT.

One aspect of the present disclosure relates methods of selectively binding and inhibiting an exogenously administered fXa inhibitor in a subject undergoing anticoagulant therapy with a fXa inhibitor comprising administering to the subject an effective amount of a solution of the lyophilized formulation. Patients suitable for this therapy have undergone prior anticoagulant therapy, for example, they have been administered one, or more of an anticoagulant, such as a direct or indirect inhibitor of fXa.

In another aspect the method provide herein selectively binds and inhibits an exogenously administered factor Xa inhibitor in a subject undergoing anticoagulant therapy with a factor Xa inhibitor comprising administering a solution of the lyophilized formulation to the subject. The subject may be a cell or a mammal, such as a human.

Subjects that will benefit from the administration of the dissolved lyophilized formulation described herein and the accompanying methods include those that are experiencing, or predisposed to a clinical major bleeding event or a clinically significant non-major bleeding event. Examples of clinical major bleeding events are selected from the group consisting of hemorrhage, bleeding into vital organs, bleeding requiring re-operation or a new therapeutic procedure, and a bleeding index of ≥2.0 with an associated overt bleed. (Turpie AGG, et al, *NEJM,* 2001, 344: 619-625.) Additionally, the subject may be experiencing or predisposed to a non-major bleeding event selected from the group consisting of epistaxis that is persistent or recurrent and in substantial amount or will not stop without intervention, rectal or urinary tract bleeding that does not rise to a level requiring a therapeutic procedure, substantial hematomas at injection sites or elsewhere that are spontaneous or occur with trivial trauma, substantial blood loss more than usually associated with a surgical procedure that does not require drainage, and bleeding requiring unplanned transfusion.

In some embodiments, the dissolved lyophilized formulation is administered after the administration of an overdose of a fXa inhibitor or prior to a surgery, which may expose subjects to the risk of hemorrhage.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1: Purification of r-Antidote from Cell Culture

This example demonstrates the development of culturing conditions and downstream purification process for manufacturing the r-Antidote. A commercial culture medium tailored for CHO cells was tested for the CHO cells transfected with a construct containing a nucleic acid sequence (SEQ ID NO: 7) that encodes an r-Antidote precursor (SEQ ID NO: 2) which, upon removal of the —RKRRKR— linker (SEQ ID NO: 6), generates the two-chain r-Antidote (SEQ ID NO: 3). The ProCHO™ medium, under suitable conditions, were able to produce a titer as high as 75-95 mg/L.

A downstream purification process ("downstream process") was developed to purify the antidote from the cultured cells. In a few initial development runs, various membranes and columns were tested.

In two test runs, the clarified harvest was found to foul the membranes when the product was concentrated by ultrafiltration (UF), or foul the chromatography media if UF was bypassed and the product was concentrated by the first chromatography step. Experiments were performed to determine the cause of the fouling and determine steps to eliminate it since concentration of the product was thought necessary early in the process. It was subsequently determined that the fouling was caused by a high molecule weight (HMW) protein impurity that was secreted into the media during cell culture. This HMW protein was only partially soluble in the clarified harvest, and upon concentration became more and more insoluble, causing unacceptable fouling of the UF membrane or chromatography column.

After an evaluation of several depth filters, ion exchange membranes, and chromatography media, it was found that one particular depth filter (Millipore™ XOHC grade filter) could remove the majority of the impurity while achieving acceptable product yield. The product could then be concentrated by UF up to 10 fold. This filter replaced one of the original filters in the clarification process and was implemented for two additional runs.

FIG. 1 illustrates the resulting purification process 100 from this development effort. After the cells are harvested (step 101) and clarified using a Millipore™ XOHC filter to remove HMW impurity, the sample is concentrated 10 fold (step 102). The concentration can use regenerated cellulose. At step 103, viral inactivation (with a detergent/solvent; final concentration: 1% Triton X-100, 0.3% Tributyl Phosphate) can be carried out to inactivate enveloped viruses in the cell culture. Following removal of the viruses, steps 104 (mixed-mode cationic exchange), 105 (mixed-mode anionic exchange) and 106 (mixed-mode ion exchange) are carried out to remove host cell proteins and DNA and capture the antidote. At step 107, a hydrophobic interaction resin can be used to further remove remaining host cell proteins. Optionally, after these purification steps, a final virus removal filtration step can be used to remove any remaining viruses.

This process was able to recover about 30-35% of the antidote expressed in the cell culture, resulting in production of about 22-33 mg of the antidote protein from each liter of cell culture.

Example 2: Scale-Up Manufacturing Process

Based on the process as shown in Example 1, a modified process was developed for the purpose of scaling up production.

The culture medium of Example 1 was able to generate a titer of about 75-95 mg/L. To increase the production, a number of other CHO culture media were tested. One of them exhibited a 2-3 fold increase in cell growth and peak cell density (titer=200-225 mg/L), and also enabled scale-up to 10,000 L.

An affinity chromatograph was developed for high-volume extraction of the antidote. The affinity ligand included Kunitz trypsin inhibitor (21 kDa; pI=4.5) extracted from whole soybean or flour. The soybean trypsin inhibitor (STI) forms 1:1 complex with the antidote. A non-competitive inhibitor elution condition was identified for scalability and compatibility, which included 25 mM Na-acetate, 1M Arginine, at pH 5.2.

In the process developed in Example 1, a harvest clarification step with a depth filter was used to remove HMW impurity, followed by a 10 fold concentration. Further, the virus inactivation step employed a detergent (Triton X-100) as well as a solvent (tributyl phosphate). The suitability and efficiency of these steps were evaluated for the affinity capture.

on clearance of affinity ligand leachate. To assess product quality and process-related impurity clearance, the same affinity eluate pool was forward processed over each stream and compared for product recovery and CHO host cell protein clearance (HCP; expressed in parts per million (ppm)). Eluates from each DSP process were additionally tested for product quality (Table below).

| | Sample | Acidic Peaks | Peak1 | Peak2 | Peak3 | Basic Peaks |
|---|---|---|---|---|---|---|
| % Peaks by IEX | Affinity Eluate | 27.8% | 17.8% | 12.91% | 16.6% | 13.9% |
| | Cation Exchange Eluate | 24.9% | 14.5% | 26.9% | 20.8% | 13.1% |
| | Mixed-Mode IEX Eluate DSP-2 | 23.4% | 15.7% | 17.3% | 20.4% | 13.3% |
| | Mixed-Mode IEX Eluate DSP-1 | 23.6% | 15.2% | 26.9% | 20.0% | 13.3% |

| | Sample | % HMW | % Monomer |
|---|---|---|---|
| % Monomer by SEC | Affinity Eluate | 0.29% | 99.71% |
| | Cation Exchange Eluate | 4.30% | 95.70% |
| | Mixed-Mode IEX Eluate DSP-2 | 0.13% | 99.87% |
| | Mixed-Mode IEX Eluate DSP-1 | 0% | 100% |

| | | Pre-Main | Main Peak | Beta Peak |
|---|---|---|---|---|
| % Main peak by RP | Affinity Eluate | 0.8% | 93.4% | 5.7% |
| | Cation Exchange Eluate | 1.2% | 92.9% | 5.9% |
| | Mixed-Mode IEX Eluate DSP-2 | 0.5% | 94.2% | 5.3% |
| | Mixed-Mode IEX Eluate DSP-1 | 0.9% | 93.4% | 5.8% |

The data show that the depth filtration was not required and that the use of a solvent and the 10× concentration step reduced the recovery of the product. Therefore, in further development, the depth filtration and the concentrating step were eliminated and the virus inactivation used a detergent only (Triton X-100), without a solvent. The virus inactivation was achieved by the addition of 10% Triton X-100 in a ratio of 52.7 ml of buffer to every liter of product (final concentration: 0.5% Triton X-100). This finding was unexpected as solvents are commonly used for sample preparation before loading to an affinity column. It is also noted that, when the cell culture was harvested, a flowing through centrifugation step was used to remove precipitates.

Following a 15 minute mixing time and a minimum of one hour hold period at room temperature, the treated product was filtered through a filter train comprised of a Sartogruad NF Filter (0.8/0.2 μm) pre-filter onto a Sartopore 2 (0.45/0.22 μm) pre-filter into a 500 L container with integral 0.22 μm filter, with each column load filtered on the day of use.

Elution of the product from the STI affinity resins used an elution buffer that contained arginine (25 mM sodium acetate/1.0 M arginine pH 5.2).

Following the affinity capture, a few polishing steps were employed to remove remaining impurities, including DNA, host cell proteins (HCP), and leachate of the affinity ligand. Two chromatography options were tested, including cation exchanger and mixed-mode ion exchange. However, there was no process-specific host cell protein assay available for characterization. Therefore, commercial ELISAs used as a surrogate, and LC-MS/MS quantitation of specific HCPs was used as supplemental characterization. Further, 2D silver stain evaluation for qualitative characterization.

Figure 3:
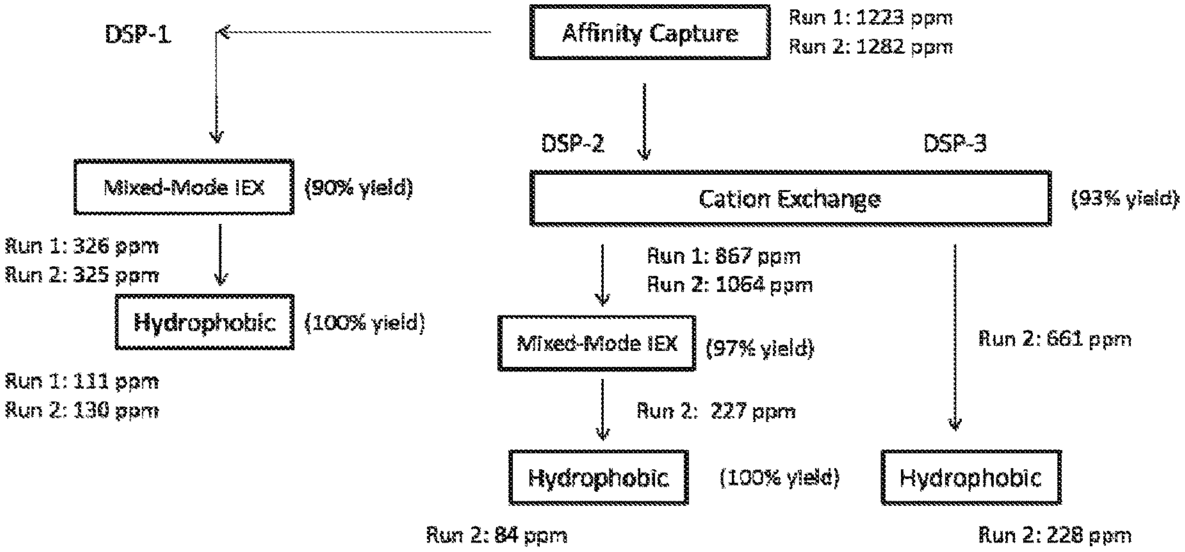
FIG. 3 shows the evaluation of three potential downstream processes (DSP).

FIG. 3 shows the evaluation of three potential downstream processes (DSP). Three DSPs were identified based Table notes: Product quality assessment of the three evaluated downstream processes. Eluates taken from the three DSPs (FIG. 3) were evaluated for product quality impact. No impact on charge-based heterogeneity (IEX) or reverse phase (RP) was seen. However, samples from DSP-2, that had been purified by a cation-exchange polishing step showed an increase in % high molecular weight aggregate, by size exclusion (SEC).

Based on the testing, a scale up downstream process was developed, which is illustrated in FIG. 2. This process is simpler than the one shown in FIG. 1. Yet, the yield was 2-fold higher. In combination with the new cell culture system that had a 2-3 fold increase of protein production, the method described in Example 2 was able to have a 4 to 6-fold increase in overall antidote production and enabled a scale of production with at least 10,000 L.

In FIG. 2, the downstream process 200 employs virus inactivation step (202), following harvest (201), that uses only a detergent (Triton X-100) without a solvent. At the affinity capture step 203, resins with a STI ligand is used, and the antidote is eluted with an elution buffer with arginine (pH 5). An optional ultrafiltration/diafiltration (UF/DF) step can be used following the affinity capture, which can concentrate the protein and bring the pH to around 7.

At step 204, an anionic membrane is used to remove certain impurity from the sample (e.g., DNA, HCPs). An example anionic membrane tested was the Sartobind Q membrane, which exhibited no detrimental effect to the antidote.

At step 205, an example type of mixed-mode ion exchange is an IEX-mixed mode with CHT (ceramic hydroxyapatite). An example elution buffer a phosphate salt buffer. This step is useful for removing STI leachate.

At step 206, hydrophobic separation can be achieved with octyl sepharose chromatography as an example, and the protein can be eluted with buffer that includes NaCl. This step is useful for removing remaining HCPs.

The following table shows the purification and recovery yield in a few test runs.

| | Bench scale (10 L) | Pilot 1 (400 L) | Pilot 2 (400 L) |
|---|---|---|---|
| Affinity Capture | 178 mg/L of cell culture | 122 mg/L of cell culture | 150 mg/L of cell culture |
| Diafiltration | 95% | 98% | 99% |
| Sartobind-Q | — | — | 95% |
| Iex-Mixed Mode | 92% | 95% | 93% |
| Hydrophobic Interaction(Octyl) | 100% | 103% | 99% |
| Viral Filtration | 95% | 92% | 94% |
| Final Uf/Df | 89% | 91% | 92% |
| Bulk Drug Substance Cumulative Yield | 60% | 69% | 66% |

Example 3: Characterization of Manufactured Protein

In this example, methods were developed to characterize the protein product generated from the above developed processes. The methods tested included isoelectric focusing (IEF), reduced reverse phase (Red-RP), and reduced peptide map (PMAP).

Isoelectric focusing was used to determine the charge heterogeneity of the antidote protein. Isoelectric focusing is an electrophoretic technique for separating proteins based on their isoelectric point (pI), or the pH at which the protein has no net charge. Isoelectric focusing was performed using pH 3-10 gels and reagents per Life Technologies manufacturer's instructions for electrophoresis (Novex IEF Gels) and staining with the Colloidal Blue Staining Kit (Invitrogen). Results were compared to Serva 3-10 pI markers.

Test lots were diluted to 1.6 mg/mL in water, then 1:1 in IEF pH 3 10 Sample Buffer. Each sample was loaded at 10 μL (8.0 lag) and electrophoresis was performed at 100 V for 1 hour followed by 200 V for 1 hour and 500 V for 30 minutes. The gels were fixed for 30 minutes in Fixing Solution (Sigma-Aldrich), stained for 1 hour in Colloidal Blue stain, and destained in water overnight.

Reduced reverse phase is a HPLC method that uses reversed phase chromatographic separation for the detection of both full-length and truncated forms of the protein. Samples were buffer exchanged into 6 M guanidine-HCl/50 mM Tris pH 7.5 and reduced with DTT prior to incubation at 50° C. for 30 minutes. The samples were then alkylated using vinylpyridine at room temperature for 90 minutes in the dark followed by quenching with 1M DTT. The method utilizes an Agilent Zorbax C18 HPLC column to bind proteins to the stationary phase and a 15 to 95% gradient of a decreasingly polar mobile phase (0.1% trifluoroacetic acid in acetonitrile) to separate proteins based on their hydrophobicity. The UV wavelength is 214 nm.

Lys-C digested Peptide Map utilized UPLC-UV/$MS^E$ analysis of Lys-C digests. This method was capable of providing over 98% sequence coverage and characterizing post translational modifications such as glycosylation, aspartate hydroxylation, and C-terminal lysine truncation. This method was also capable of monitoring stability-indicating markers such as asparagine deamidation and methionine oxidation. Sample lots were each reduced, alkylated and treated with Lysyl endopeptidase (Lys-C). The peptides generated by the enzymatic digestion were separated by RP-UPLC and analyzed by mass spectroscopy.

The following tables show the type of protein isoforms detected from the purified protein products and their percentages and sequences (Lot #1: with downstream process developed in Example 1; Lot #1: with downstream process developed in Example 2). It is interesting to note that, compared to the process of Example 1, the process of Example 2 considerably reduced the percentage of SEQ ID NO: 9 (from 9.0% to 2.7%), likely due to increased purification efficiency.

Light Chain Isoforms:

| | Lot #1 | Lot #2 |
|---|---|---|
| Intact light chain (SEQ ID NO: 4) | 46.8% | 37.9% |
| Modified or truncated light chain | 53.2% | 62.1% |

Heavy Chain Isoforms:

| | Lot #1 | Lot #2 |
|---|---|---|
| Intact heavy chain (SEQ ID NO: 5) with 2 O-linked glycosylation | 10.2% | 22.0% |
| Intact heavy chain (SEQ ID NO: 5) with 1 O-linked glycosylation | 18.3% | 22.6% |
| C-terminal K truncated (SEQ ID NO: 8) with 1 O-linked glycosylation | 57.8% | 46.9% |
| Loss of 13 C-terminal residues (SEQ ID NO: 9) | 9.0% | 2.7% |
| Loss of 14 C-terminal residues (SEQ ID NO: 10) | 0.6% | 0.8% |
| Loss of 15 C-terminal residues (SEQ ID NO: 11) | 4.0% | 5.0% |

```
Heavy Chain without C-terminal K
                                                         (SEQ ID NO: 8)
181                IVGGQE CKDGECPWQA LLINEENEGF CGGTILSEFY ILTAAHCLYQ

241  AKRFKVRVGD RNTEQEEGGE AVHEVEVVIK HNRFTKETYD FDIAVLRLKT PITFRMNVAP

301  ACLPERDWAE STLMTQKTGI VSGFGRTHEK GRQSTRLKML EVPYVDRNSC KLSSSFIITQ

361  NMFCAGYDTK QEDACQGDAG GPHVTRFKDT YFVTGIVSWG EGCARKGKYG IYTKVTAFLK

421  WIDRSMKTRG LPKAKSHAPE VITSSPL

Heavy Chain without 13 C-terminal residues
                                                         (SEQ ID NO: 9)
181                IVGGQE CKDGECPWQA LLINEENEGF CGGTILSEFY ILTAAHCLYQ
```

-continued

```
241  AKRFKVRVGD RNTEQEEGGE AVHEVEVVIK HNRFTKETYD FDIAVLRLKT PITFRMNVAP

301  ACLPERDWAE STLMTQKTGI VSGFGRTHEK GRQSTRLKML EVPYVDRNSC KLSSSFIITQ

361  NMFCAGYDTK QEDACQGDAG GPHVTRFKDT YFVTGIVSWG EGCARKGKYG IYTKVTAFLK

421  WIDRSMKTRG LPKAK
```

Heavy Chain without 14 C-terminal residues

```
                                                      (SEQ ID NO: 10)
181               IVGGQE CKDGECPWQA LLINEENEGF CGGTILSEFY ILTAAHCLYQ

241  AKRFKVRVGD RNTEQEEGGE AVHEVEVVIK HNRFTKETYD FDIAVLRLKT PITFRMNVAP

301  ACLPERDWAE STLMTQKTGI VSGFGRTHEK GRQSTRLKML EVPYVDRNSC KLSSSFIITQ

361  NMFCAGYDTK QEDACQGDAG GPHVTRFKDT YFVTGIVSWG EGCARKGKYG IYTKVTAFLK

421  WIDRSMKTRG LPKA
```

Heavy Chain without 15 C-terminal residues

```
                                                      (SEQ ID NO: 11)
181               IVGGQE CKDGECPWQA LLINEENEGF CGGTILSEFY ILTAAHCLYQ

241  AKRFKVRVGD RNTEQEEGGE AVHEVEVVIK HNRFTKETYD FDIAVLRLKT PITFRMNVAP

301  ACLPERDWAE STLMTQKTGI VSGFGRTHEK GRQSTRLKML EVPYVDRNSC KLSSSFIITQ

361  NMFCAGYDTK QEDACQGDAG GPHVTRFKDT YFVTGIVSWG EGCARKGKYG IYTKVTAFLK

421  WIDRSMKTRG LPK
```

Example 4: Validation of Scaled-Up Process

This example describes a process based on the processes as shown in Examples 1 and 2 for further validation.

Viral Inactivation by Detergent

The Viral inactivation step was performed by adding 10% Triton X-100 to the harvested protein. The harvested protein corresponding to 1 Capto STI cycle (as described below) was filtered from the Harvest tank to the 10% Triton X-100 addition tank through 4×30" Sartoguard NF filters that were used as pre-filters and then filtered through 3×20" Sartoguard NF Filters 0.8/0.2 μm. After the 10% Triton X-100 addition the pool was mixed and then transferred to the Hold tank through 3×30" Sartoguard NF 0.8/0.2 μm filters. Once the Hold time was completed the inactivated pool is loaded onto the Capto STI column through 6×30" Sartoguard NF Filter 0.8/0.2 μm filters in series with 3×30" Sartopore 2 0.45/0.2 μm filters. This sequence was repeated until the 4 cycles to be performed during the Capto STI operation were completed. The 6×30" Sartoguard NF 0.8/0.2 μm filters were replaced after the second cycle is loaded.

Capto STI Chromatography

Affinity column chromatography was performed using Capto STI resin at ambient temperature. During the load phase, the product bound to the resin while contaminants flew through. The product was recovered by disrupting protein interactions with a high concentration of arginine in the elution buffer. Prior to use, the column was rinsed with water for injection (WFI), cleaned with 100 mM Phosphoric Acid pH 3.0, and rinsed with WFI. The column was initially pre-equilibrated with pre-equilibration buffer (20 mM Tris-HCl, pH 7.4), then equilibrated with equilibration buffer (20 mM Tris-HCl, 200 mM NaCl, pH 7.4), and once the pH and conductivity of the column were within specification, it was loaded with Triton-X 100 treated clarified harvest (HCCF). Each cycle of HCCF material was transferred from its viral inactivation hold tank directly to the column.

Following the load, the column was washed with the equilibration buffer, and eluted with high arginine lower pH elution buffer (elution buffer: 25 mM Sodium acetate 1.0M Arginine pH 5.2). At the end of the cycle, and before the next cycle, the column was rinsed with WFI, cleaned again with 100 mM Phosphoric Acid pH 3.0, and rinsed again with WFI. All eluates coming from several cycles were pooled together. After the last cycle was collected, a buffer chase was done, bypassing the column, in order to flush the eluted product from the lines downstream of the column into the collection vessel. After all cycles were completed, the column was rinsed with WFI, cleaned with 100 mM Phosphoric Acid pH 3.0, rinsed with WFI, neutralized with pre equilibration and equilibration buffer and stored in ethanol storage solution.

The Capto STI eluate pool was mixed with 1.0M Arginine HCl pH 7.0 to a final concentration of 100 mM Arginine HCl to stabilize the pool. The resulting pool was then concentrated and diafiltered on a 10 KDa Ultracel Pellicon 3 membrane to remove the majority of the arginine, permitting loading on to the subsequent chromatography steps.

Sartobind Q Membrane Chromatography

The anion exchange membrane chromatography was performed using a Sartobind Q Jumbo cartridge at ambient temperature. During the load phase the product flew through the membrane while contaminants bind. Prior to use the cartridge was rinsed with equilibration buffer to remove the storage humectant. The cartridge was cleaned with 0.5M NaOH. The cartridge was then equilibrated with equilibration buffer and, once the pH and conductivity of the cartridge were within specification, it was loaded with concentrated, diafiltered Capto STI eluate. One cycle of load material was directly loaded from the post UF/DF collection tank. Following the load, the cartridge was washed with the equilibration buffer. After the product was collected, a buffer chase was done, bypassing the cartridge, in order to flush the product from the lines downstream of the cartridge into the collection vessel.

Ceramic Hydroxyapatite Chromatography (CHT)

The mixed mode column chromatography was performed using CHT Type I 40 m resin at ambient temperature. During the load phase, the product bound to the resin whilst some contaminants flew through. The product was recovered by increasing the sodium concentration in a linear gradient. Prior to use, the column was cleaned with 1.0M NaOH and rinsed with a small volume of equilibration buffer. The column was initially pre-equilibrated with pre-equilibration buffer, and then equilibrated with equilibration buffer, and once the pH and conductivity of the column were within specification, it was loaded with Sartobind Q eluate.

Each cycle of Load was transferred from its collection tank directly to the column. Following the load, the column was washed with the equilibration buffer. A gradient was then run from 90% equilibration buffer (50 mM MES, 5 mM Sodium Phosphate, pH 7.0) to 90% elution buffer (50 mM MES, 5 mM Sodium Phosphate, 2M Sodium Chloride pH 7.0).

At the end of the cycle, and before the next cycle, the column was rinsed with equilibration buffer before being stripped with high phosphate post elution wash buffer, rinsed with equilibration buffer, cleaned again with 1.0M NaOH, and rinsed again with equilibration buffer. All eluates coming from several cycles were pooled together. After the last cycle was collected, a buffer chase was done, bypassing the column, in order to flush the eluted product from the lines downstream of the column into the collection vessel. After all cycles were completed, the column was rinsed with equilibration buffer, cleaned with 1.0M NaOH, and stored in caustic/phosphate storage solution.

Octyl Sepharose 4FF Chromatography

The hydrophobic interaction chromatography was performed using Octyl Sepharose FF resin at ambient temperature. During the load phase the product flew through the resin whilst contaminants bound. Prior to use the column was cleaned with 1.0M NaOH. The column was initially pre-equilibrated with WFI, and then equilibrated with equilibration buffer, and once the pH and conductivity of the column were within specification, it was loaded with CHT eluate. Each cycle of Load was transferred from its collection tank directly to the column. Following the load, the column was washed with the equilibration buffer. At the end of the cycle, and before the next cycle, the column was stripped with WFI, and cleaned again with 1.0M NaOH. After the last cycle was collected, a buffer chase was done, bypassing the column, in order to flush the product from the lines downstream of the cartridge into the collection vessel. After all cycles were completed, the column was stripped with WFI, cleaned with 1.0M NaOH, and stored in caustic storage solution.

Planova 20N Viral Reduction Filtration (VRF)

The virus reduction filtration was performed on a Planova 20N virus reduction filter. The filter was operated in dead end mode, the product passed through the filter whilst any remaining viral particles were retained in the fibres. The filter was flushed with the Octyl Sepharose equilibration buffer before use. The product was then passed through the filter and then flushed with additional equilibration buffer. The filter was tested for integrity and disposed of after use.

The VRF filtrate was concentrated on a 10 KDa Ultracel Pellicon 3 membrane. After partial concentration it as diafiltered into the final formulation. The product was then concentrated to the final target concentration and recovered.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms “comprising”, “including,” “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A pharmaceutical composition comprising a pharmaceutically acceptable carrier and a plurality of two-chain polypeptides obtainable by processing a precursor comprising the amino acid sequence of SEQ ID NO:2 and comprising a light chain and a heavy chain, wherein:

about 35%-60% of the light chains consist of the amino acid sequence of SEQ ID NO: 4;

about 20%-60% of the heavy chains consist of the amino acid sequence of SEQ ID NO: 5;

about 40%-60% of the heavy chains consist of the amino acid sequence of SEQ ID NO: 8; and less than 10% of heavy chains consist of the amino acid sequence of SEQ ID NO: 9.

2. The pharmaceutical composition of claim 1, wherein less than 5% of the heavy chains consist of the amino acid sequence of SEQ ID NO: 9.

3. The pharmaceutical composition of claim 1, wherein less than 3% of heavy chains consist of the amino acid sequence of SEQ ID NO: 9.

4. The pharmaceutical composition of claim 1, which does not include soybean trypsin inhibitor (STI).

5. The pharmaceutical composition of claim 1, wherein about 0.1%-1.5% of the two-chain polypeptides have a heavy chain consisting of the amino acid sequence of SEQ ID NO: 10.

6. The pharmaceutical composition of claim 1, wherein about 2%-8% of the two-chain polypeptides have a heavy chain consisting of the amino acid sequence of SEQ ID NO: 11.

7. The pharmaceutical composition of claim 1, wherein about 30%-70% of the heavy chain consisting of the amino acid sequence of SEQ ID NO: 5 has two O-linked glycosylations.

8. The pharmaceutical composition of claim 1, wherein about 30%-70% of the heavy chain consisting of the amino acid sequence of SEQ ID NO: 5 has one O-linked glycosylation.

9. The pharmaceutical composition of claim 1, wherein at least about 90% of the heavy chain consisting of the amino acid sequence of SEQ ID NO: 8 has one O-linked glycosylation.

10. The pharmaceutical composition of claim 1, wherein the preparation is lyophilized.

11. The pharmaceutical composition of claim 1, further comprising L-arginine HCl or L-arginine acetate.

12. The pharmaceutical composition of claim 1, further comprising sucrose.

13. The pharmaceutical composition of claim 1, further comprising mannitol.

14. A method for reversing or inhibiting anticoagulation in a patient undergoing an anticoagulation treatment with a factor Xa inhibitor, comprising administering to the patient a pharmaceutical composition of claim 1.

* * * * *

SEQUENCE LISTING

<160> NUMBER OF SEQ ID NOS: 11

<210> SEQ ID NO 1
<211> LENGTH: 448
<212> TYPE: PRT

<213> ORGANISM: Homo sapiens

<400> SEQUENCE: 1

```
Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
    370                 375                 380

Thr Arg Phe Lys Asp Thr Tyr Phe Val Thr Gly Ile Val Ser Trp Gly
385                 390                 395                 400
```

-continued

```
Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445


<210> SEQ ID NO 2
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
    290                 295                 300

Lys Asp Thr Tyr Phe Val Thr Gly Ile Val Ser Trp Gly Glu Gly Cys
305                 310                 315                 320
```

```
Ala Arg Lys Gly Lys Tyr Gly Ile Tyr Thr Lys Val Thr Ala Phe Leu
                325                 330                 335

Lys Trp Ile Asp Arg Ser Met Lys Thr Arg Gly Leu Pro Lys Ala Lys
            340                 345                 350

Ser His Ala Pro Glu Val Ile Thr Ser Ser Pro Leu Lys
        355                 360                 365


<210> SEQ ID NO 3
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
```

-continued

```
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
        355


<210> SEQ ID NO 4
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg
            100                 105


<210> SEQ ID NO 5
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
```

-continued

```
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250


<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Lys Arg Arg Lys Arg
1               5


<210> SEQ ID NO 7
<211> LENGTH: 1218
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

atggggcgcc cactgcacct cgtcctgctc agtgcctccc tggctggcct cctgctgctc      60

ggggaaagtc tgttcatccg cagggagcag gccaacaaca tcctggcgag ggtcacgagg     120

gccaattcct ttcttttctg gaataaatac aaagatggcg accagtgtga gaccagtcct     180

tgccagaacc agggcaaatg taaagacggc ctcggggaat acacctgcac ctgtttagaa     240

ggattcgaag gcaaaaactg tgaattattc acacggaagc tctgcagcct ggacaacggg     300

gactgtgacc agttctgcca cgaggaacag aactctgtgg tgtgctcctg cgcccgcggg     360

tacaccctgg ctgacaacgg caaggcctgc attcccacag ggccctaccc ctgtgggaaa     420

cagaccctgg aacgcaggaa gaggaggaag aggatcgtgg gaggccagga atgcaaggac     480

ggggagtgtc cctggcaggc cctgctcatc aatgaggaaa acgagggttt ctgtggtgga     540

accattctga gcgagttcta catcctaacg gcagcccact gtctctacca agccaagaga     600

ttcaaggtga gggtagggga ccggaacacg gagcaggagg agggcggtga ggcggtgcac     660

gaggtggagg tggtcatcaa gcacaaccgg ttcacaaagg agacctatga cttcgacatc     720

gccgtgctcc ggctcaagac ccccatcacc ttccgcatga acgtggcgcc tgcctgcctc     780

cccgagcgtg actgggccga gtccacgctg atgacgcaga agacggggat tgtgagcggc     840

ttcgggcgca cccacgagaa gggccggcag tccaccaggc tcaagatgct ggaggtgccc     900

tacgtggacc gcaacagctg caagctgtcc agcagcttca tcatcaccca gaacatgttc     960
```

-continued

```
tgtgccggct acgacaccaa gcaggaggat gcctgccagg gggacgcagg gggcccgcac   1020

gtcacccgct tcaaggacac ctacttcgtg acaggcatcg tcagctgggg agagggctgt   1080

gcccgtaagg ggaagtacgg gatctacacc aaggtcaccg ccttcctcaa gtggatcgac   1140

aggtccatga aaaccagggg cttgcccaag gccaagagcc atgccccgga ggtcataacg   1200

tcctctccat taaagtga                                                 1218
```

<210> SEQ ID NO 8
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu
                245                 250
```

<210> SEQ ID NO 9
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 9

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys

<210> SEQ ID NO 10
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg

-continued

```
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240


<210> SEQ ID NO 11
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220
```

-continued

```
Leu Lys Trp Ile Asp Arg Ser Met Lys Thr Arg Gly Leu Pro Lys
225                 230                 235
```